United States Patent [19]

Firestone

[11] Patent Number: 4,560,512

[45] Date of Patent: Dec. 24, 1985

[54] DERIVATIVES OF STEROID COMPOUNDS LINKED TO CYOTOXIC AGENTS

[75] Inventor: Raymond A. Firestone, Fanwood, N.J.

[73] Assignee: Merck & Co., Inc., Rahway, N.J.

[21] Appl. No.: 580,507

[22] Filed: Feb. 15, 1984

Related U.S. Application Data

[63] Continuation of Ser. No. 431,943, Sep. 30, 1982, abandoned.

[51] Int. Cl.[4] .................................................. C07J 7/00
[52] U.S. Cl. .............................. 260/397.2; 260/397.1; 260/397.5
[58] Field of Search ........................... 260/397.2, 397.1

[56] References Cited

U.S. PATENT DOCUMENTS 4,104,285 8/1978 Torres et al. ...................... 260/397.1
4,372,888 2/1983 Hjelmeland ....................... 260/397.1

OTHER PUBLICATIONS

J. Med. Chem. (1984) 27(8) pp. 1037–1043, an article by Firestone et al.

*Primary Examiner*—Elbert L. Roberts
*Attorney, Agent, or Firm*—Thomas E. Arther; Daniel T. Szura; Hesna J. Pfeiffer

[57] ABSTRACT

The present application is concerned with compounds useful as carriers of cytotoxic agents. More particularly it deals with derivatives of steroid compounds having a 5-androstene carbon skeleton and having an oleyl ester at the 3-position and having a 17-carbamyl alkyl substituent which linked to cytotoxic agents for delivery to cancer cells exclusively via the low-density lipoprotein (LDL) pathway.

6 Claims, No Drawings

DERIVATIVES OF STEROID COMPOUNDS LINKED TO CYOTOXIC AGENTS

This is a continuation of application Ser. No. 431,943, filed Sept. 30, 1982, now abandoned.

BACKGROUND OF THE INVENTION

It is known that low density lipoprotein (LDL) particles are important factors in the regulation of plasma cholesterol. The cholesterol is transmitted as either of two types of liquids: (1) triglycerides of cholesterol or (2) long chain fatty acid esters of cholesterol. The LDL particles are small blood-borne lipid encased spheres which ordinarily contain a cholesterol ester as a hydrophobic core. The surface of the LDL particles is composed of certain phospholipids, free cholesterol and apoproteins which direct the particle to the site of metabolism (*Regulation of Plasma Cholesterol by Lipoprotein Receptors*, Brown et al., *Science*, Vol. 212, p. 628,, May 8, 1981.

It is also known prior to the present invention that LDL particles ca be broken open to remove the contents and then reconstituted with different materials incorporated into the core of the LDL particles. This reconstitution with different core material does not always provide stable LDL particles but in some instances provides LDL particles which give up the core material before arriving at the intended site. In an ideal situation, the reconstituted LDL particles incorporating the desired material are targeted to the cells and taken up by the cells by endocytosis whereupon the core material is released into the target cell. In this connection, certain cancer cells have extremely high requirements for LDL compared to normal body cells.

One of the objects of the present invention is to provide new compounds which are effective as cytotoxic agents.

Another object is to provide compounds which are readily incorporated into the core of LDL particles and which are stable until incorporated into the target cells.

A still further object is the provision of non-toxic derivative of a steroid compound and a cytotoxic agent which is readily hydrolyzed intracellularly thereby providing a killing dose of the cytotoxic agent within the target cells. These and other objects are accomplished by applicants' discovery which is described in greater detail hereinbelow.

DESCRIPTION OF THE INVENTION

This invention relates to compounds which are steroid derivatives of cytotoxic agents wherein said steroids have the basic carbon skeleton of androstene, esterified at the 3-hydroxy position by a long chain (12-20 carbons) unsaturated fatty acid and having a 17-side chain consisting of an alkyl carbamoyl radical linked through an amido nitrogen to a cytotoxic substance such as a nitrogen mustard compound.

More particularly, the present invention relates to steroid esters of the formula:

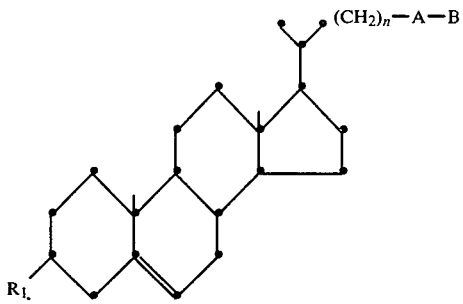

wherein $R_1$ is an unsaturated aliphatic carbonyloxyl radical of from 12-20 carbons n is an integer of from 1-10

A is a bivalent linking radical selected from (a)

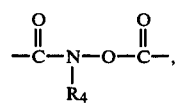

wherein $R_4$ is H, lower alkyl, phenyl or heteroaryl.

(b)

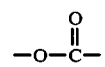

(c)

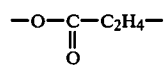

(d)

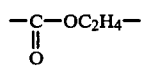

and

B is a radical derived from a cytotoxic substance linked through an amino substituent wherein said cytotoxic substance is selected from, uracil mustard, 6-mercaptopurine, thioguanine, adriamycin, procarbazine, nitromycin and bis-(2-chloroethyl)amine.

Still more specifically the invention comprises 3-oleyl esters of 3-hydroxy-5-androstenes having a 17-position side chain comprising a 2-pentyl radical linked through a carbamate linkage to a cytotoxic agent.

The nitrogen atom of the carbamate linkage can form part of the cytotoxic moiety of applicants' novel steroid compounds. Thus, for example, a preferred compound of applicants' invention is 2(3β-oleoyloxy-androst-5-enyl) 17β-pentyloxycàrbonyl bis(2-chloroethyl)amine of the formula:

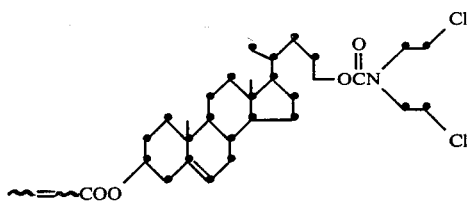

It has been found that these compounds of applicants' invention can be incorporated into LDL particles replacing cholesterol esters naturally present in the core of the LDL particles using known procedures as set forth in the published literature; *Replacement of Endogenous Cholesteryl Esters of Low Density Lipoprotein With Endogenous Cholesteryl Linoleate,* Krieger, M., M. S. Brown, J. R. Faust and J. L. Goldstein (1978); *Reconstitution of a Biologically Active Lipoprotein Particle, J. Biol. Chem.* 253:4093–4141, Krieger, M., M. J. McPhaul, J. L. Goldstein, and M. S. Brown (1979) Replacement of Neutral Lipids of Low Density Lipoprotein With Esters of Long-Chain Unsaturated Fatty Acids, *J. Biol. Chem.,* 254:3845–3853.

The reconstitution procedure whereby applicants' novel compounds can be incorporated into LDL particles for delivery to cells having high requirement for LDL particles involves several steps. The LDL solution is first dialyzed under sterile conditions to remove undesirable low molecular weight impurities. The LDL material diluted with water is then frozen and lyophilized to open the LDL particle and release the cholesterol esters contained therein. The resulting lyophilized material is then extracted with heptane to remove a substantial amount of cholesteryl esters and leave the remainder of the LDL particles as a residue. An appropriate amount of one of applicants' compounds dissolved in heptane is then added to the LDL residue and the mixture incubated for approximately 1 hour at 10° C. The heptane is removed from the mixture and the residue diluted with buffers and incubated for several hours at 4° C. to produce reconstituted LDL particles wherein applicants' compound is incorporated into the core of the LDL particles. At this stage the reconstituted LDL particles are suspended in the aqueous buffer solution and are separated by centrifugation leaving the LDL particles as a semisolid pellet from which the supernatant buffer solution may be removed by aspiration. The semisolid pellet of reconstituted LDL may then be formulated into pharmaceutical composition suitable for parenteral administration.

The compounds of the present invention are prepared by reaction of a steroid compound of the formula:

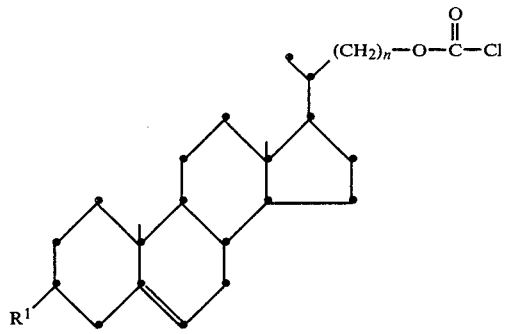

wherein $R^1$ and n are defined as hereinabove and a cytotoxic agent containing an amine group to produce a compound of the formula:

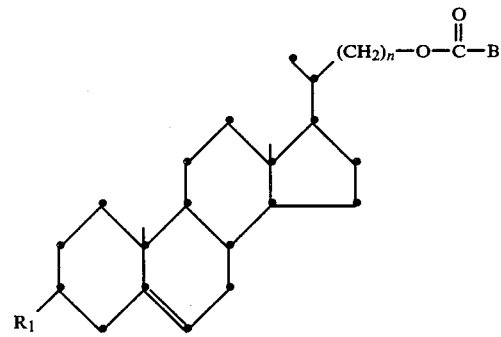

wherein $R_1$, n and B are as defined hereinabove.

Examples of compounds within the scope of applicants' invention include: 3-β-oleoyl, 3β-linoleoyl and 3β-linolenoyl esters of 3β-hydroxy 5-androstene compounds having a 17-side chain comprising a 2-alkyloxycarbonyl substituent linked to an amino substituent of a cytotoxic compound.

Especially preferred compounds of the present invention are: 2(3β-oleoyloxy-androst-5-ene-17β-yl)propyloxycarbonyl bis(2-chloroethyl)amine; 4-(3β-oleoyloxy-androst-5-en-17β-yl)pentyloxycarbonyl bis(2-chloroethyl)amine.

Other compounds included within the scope of the present invention are corresponding derivatives of the above steroid esters in which the bis(2-chloroethyl)amine substituent is replaced by another cytotoxic substance selected from fluorouracil of the structure:

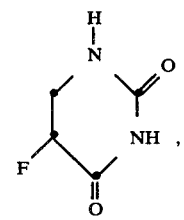

uracil mustard, 6 mercaptopurine, or thioguanine.

The compounds of applicants' invention are useful in the selective killing of cells in vivo or in vitro when incorporated into the core of LDL particles which are selectively absorbed by cells via endocytosis and the cytotoxic substance released by intracellular hydrolysis.

The present invention comprises novel cytotoxic compositions useful in the selective killing of certain specific cells. These novel compositions include a pharmaceutical carrier for intravenous administration and a therapeutically effective amount of a steroid ester of the formula:

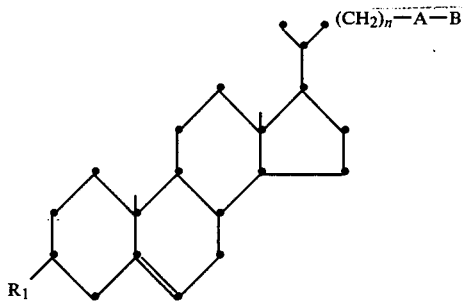

wherein $R_1$, n, A and B are as defined as in Formula I hereinabove, said steroid ester being incorporated into the core of reconstituted LDL particles.

EXAMPLE 1

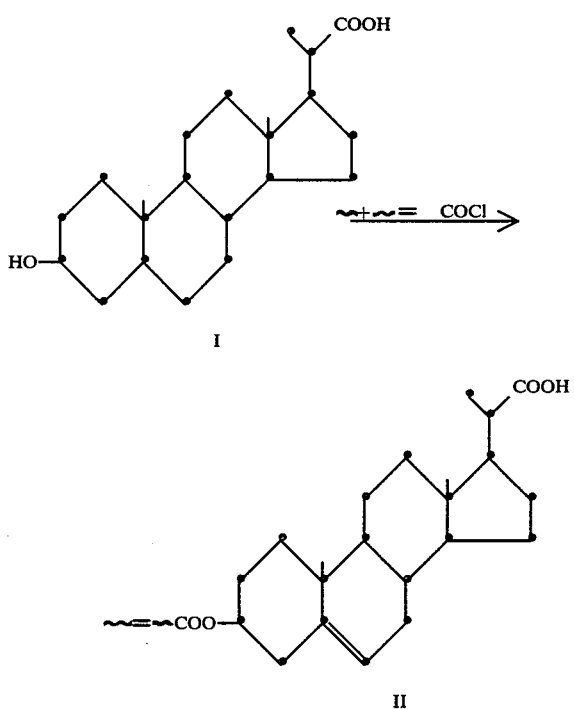

22,23-bisnorcholen-5-ic acid 3β-oleate (II)

Compound I, 22,23-bisnorcholen-5-ic acid, 173 mg (0.5 mMol) and 122 mg (1 mMol) 4-dimethylaminopyridine in 2 ml pyridine are treated with 150 mg oleoyl chloride (0.5 mMol) 2 hours at 25° and 15 min. at 100°. The solvent is evaporated i.v. The residue is taken up in CHCl₃, washed with aq. H₃PO₄ and brine, dried with MgSO₄, filtered and evaporated i.v. to give 333 mg II. IR (μ): 5.75 (ester), 5.85 (COOH); the 5.85 band disappears on addition of morpholine. MS of Me ester (CH₂N₂): 625. NMR ( ): 4.6 (C$\underline{H}$OOC₁₈H₃₃).

EXAMPLE 2

22,23-bisnorcholen-5-ic acid chloride 3β-oleate (III)
(10143-129)

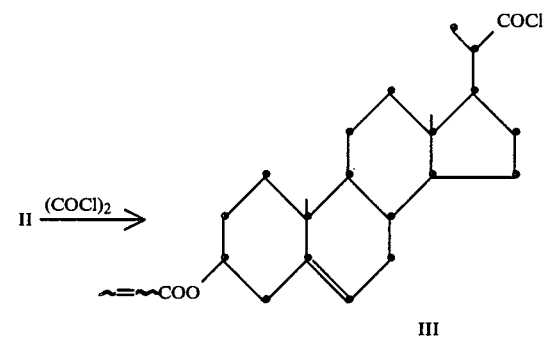

To 243 mg cpd II (0.398 mMol) in 1.5 ml CH₂Cl₂ is added 0.040 ml oxalyl chloride (0.469 mMol) and 0.0008 ml DMF. After 1.8 hrs. at 25°, the solvent is evaporated i.v., affording 224 mg III. IR (μ): 5.56 (COCl), 5.75 (ester).

EXAMPLE 3

2-(3β-oleoyloxy-androst-5-enyl)-propanol (IV)
(10143-140)

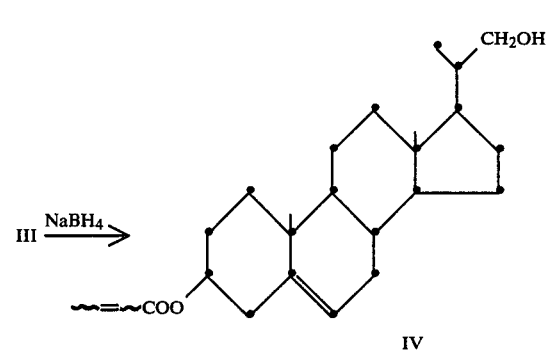

Cpd III (3.29 mMol) in 5 ml dioxane is added to 152 mg NaBH₄ (4 mMol) in 5 ml dioxane over 7 min. The reaction is aged 5 min at 25° and 10 min at 100°, and then evaporated i.v. and treated successively with water, aq HCl, and K₂HPO₄ to neutrality. The mixture is extracted twice with CH₂Cl₂, which is washed with brine, dried with MgSO₄, filtered and evaporated i.v., affording 1.949 g crude IV. Of this, 436 mg is chromatographed by PLC on silica gel, eluting with 50:1 CHCl₃-EtOAc, Rf 0.4, providing 230 mg pure IV. MS: 596. NMR: 3.6 (C$\underline{H}_2$OH).

EXAMPLE 4

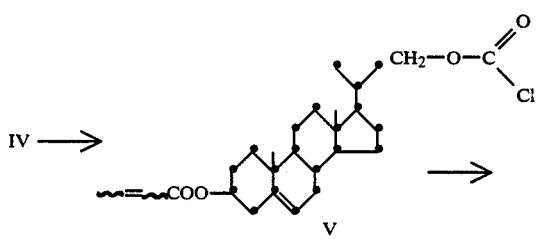

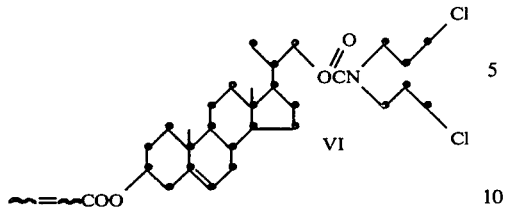

2-(3β-oleoyloxy-androst-5-en-17β-yl)-propyloxycarbonyl bis(2-chloroethyl)amine (VI) (10589-221)

To 271 mg IV (0.45 mMol) in 10 ml ether is added 3 ml phosgene (1.7M in benzene). The mixture is aged 30 min. at 25° and evaporated i.v., leaving V. To this is added 0.45 mMol each of $HN(CH_2CH_2Cl)_2$ and 4-dimethylaminopyridine (DMAP) and the mixture aged 3 days. Ethyl acetate is added and the organic layer is washed with water, aq $K_2HPO_4$ and brine, dried with $K_2CO_3$, filtered, evaporated, and chromatographed by PLC on silica gel, using 50:1 $CHCl_3$-EtOAc, affording 148 mg VI. NMR: 3.6, 8H $(NC\underline{H}_2C\underline{H}_2Cl)_2$. MS: 481 $Cl_2$ $(M^+-C_{18}H_{33}O_2)$.

EXAMPLE 5

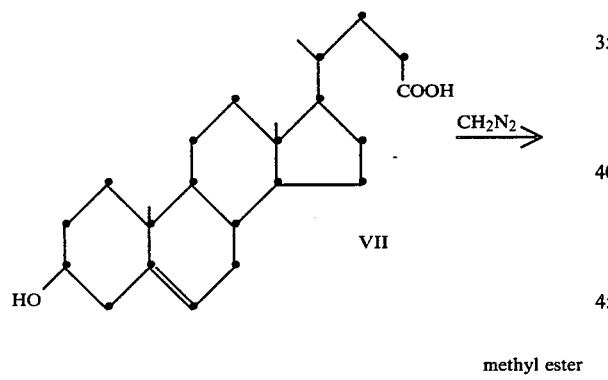

Methyl 3β-hydroxy cholen-5-ate (VIII) (10143-245)

Compound I, 3β-hydroxy cholen-5-ic acid, 5.31 g, is treated with diazomethane in 100 ml 1:1 $CHCl_3$-EtOH until the yellow color persists, then dropwise with AcOH until colorless. The soluiton is washed with aq $Na_2CO_3$ and brine, dried with $MgSO_4$, filtered and evaporated, leaving 5.399 g VIII, NMR ( , $CDCl_3$): 3.6 $(COOC\underline{H}_3)$. 3.5 $(C\underline{H}OH)$. MS: 388.

EXAMPLE 6

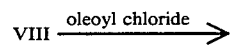

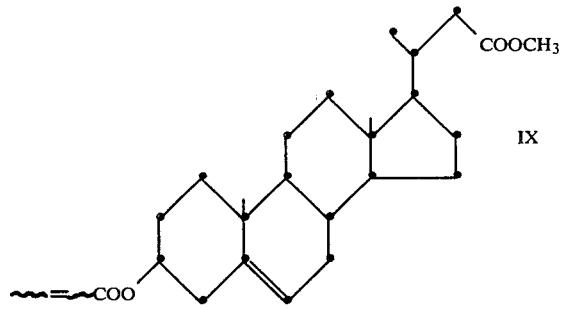

Methyl 3β-oleoyloxy cholen-5-ate (IX) (10143-233)

To cpd VIII, 598 mg (1.54 mMol) in 10 ml $CH_2Cl_2$, is added 198 mg DMAP (1.62 mMol) and then 464 mg oleoyl chloride (1.54 mMol) in 5 ml $CH_2Cl_2$. The mixture is stirred at 25° for 17 hrs and then treated with water, washed with aq $H_3PO_4$, water and sat. aq. $Na_2CO_3$, dried successively with $K_2CO_3$ and $MgSO_4$, filtered and evaporated, affording 997 mg IX as an oil. IR: C=O at 5.73μ only. NMR: 4.6 $C\underline{H}OCOC_{17}H_{33}$. MS: 652.

EXAMPLE 7

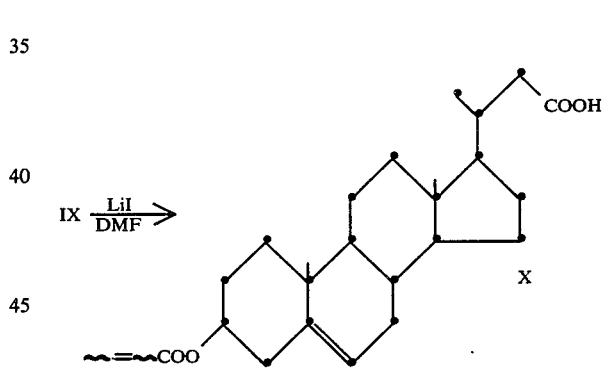

3β-Oleoyloxy cholen-5-ic acid (X) (10143-234)

Cpd IX, 103 mg, is refluxed 6 hrs in 28 ml DMF with 497 mg LiI, slowly distilling out 25 ml during the first 4 hrs. The residue is cooled, diluted with ether, washed with 1N HCl, water 3x, and brine, dried with $MgSO_4$, filtered and evaporated, giving 108 mg X containing about 10% unreacted IX. MS: 638. NMR: 3.6 almost gone.

EXAMPLE 8

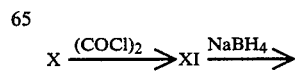

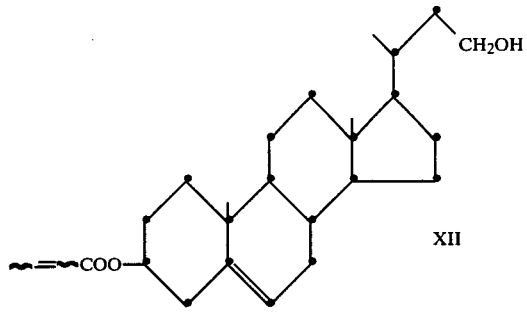

4-(3β-oleoyloxy-androst-5-en-17-yl)-pentanol (XII) (10143-235)

Cpd X, 108 mg in 1 ml CH₂Cl₂, is treated with 0.050 ml oxalyl chloride and 0.001 ml DMF 1 hr, and then evaporated, yielding XI. IR: 5.54, 5.75 (COCl and ester). The sample is flushed once with benzene, taken up in 1.5 ml dioxane, and treated with 37 mg NaBH₄ 5 min at 25° and 10 min at 100°. The mixture is cooled to 0°, treated with water, acidified with HCl, neutralized with K₂HPO₄ and extracted 2x with CH₂Cl₂. The organic extracts are washed with brine, dried with MgSO₄, filtered, evaporated and chromatographed on silica gel by PLC, eluting with 50:1 CHCl₃-EtOAc, Rf=0.5, affording 52 mg pure XII. MS: 624. NMR: 3.6 (C$\underline{H}$₂OH).

EXAMPLE 9

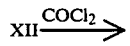

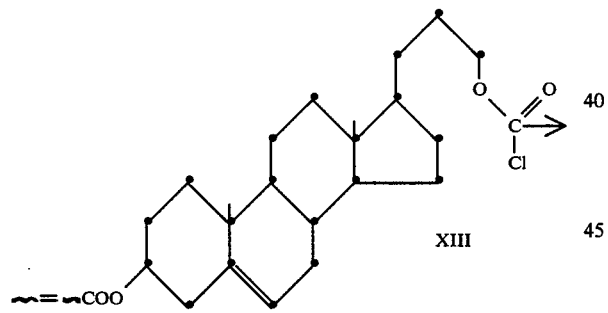

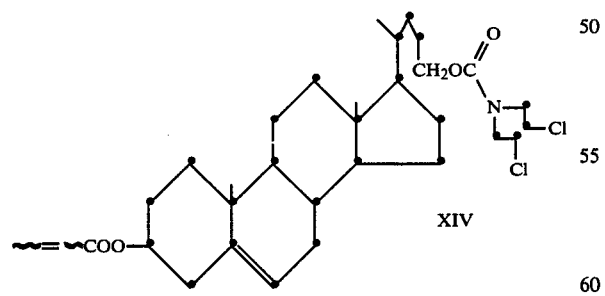

4-(3β-oleoyloxy-androst-5-en-17-yl)-pentyloxycarbonyl bis(2-chloroethyl)amine (XIV) (10143-237)

Cpd XII, 33 mg, is treated with 1 ml phosgene (1.7M in benzene) 16 hrs at 25°. Evaporation i.v. of solvent leaves XIII. IR: 5.61, 5.76 (COCl and ester). To cpd XII in 1 ml benzene is added 0.090 ml HN(CH₂CH₂Cl)₂ and 13 mg 4-dimethylaminopyridine (DMAP). After 3 hrs at 25° the reaction mixture is treated with water and washed with aqueous H₃PO₄, water, aq K₂HPO₄ and brine, dried with MgSO₄, filtered, evaporated and chromatographed by PLC on silica gel, eluting with CHCl₃ (Rf=0.6) to give 29 mg pure XIV. MS: 792, 793, 794. NMR: 4.1 (C$\underline{H}$₂OCONR₂), 3.7 (NHC$\underline{H}$₂CH₂Cl)₂.

EXAMPLE 10

Pharmaceutical Dosage Forms

In accordance with the procedure described on page 5, line 1 to page 6, line 11, the following materials are prepared and each diluted to 100 ml with sterile distilled water:

(a) 1000 mg reconstituted LDL containing 350 mg 2-(3β-oleoyloxy-androst-5-ene-17β-yl)propyloxycarbonyl-bis-(2-chloroethyl)amine as the active core ingredient in 100 ml sterile distilled water;

(b) 1000 mg reconstituted LDL containing 350 mg 4-(3β-oleoyloxy-androst-5-ene-17β-yl)-pentyloxycarbonyl-bis-(2-chloroethyl)amine as the active core ingredient in 100 ml sterile distilled water.

Each of the above aqueous dispersions comprise a typical daily dose for a patient weighing approximately 70 kg. This dose is adjusted based on patient weight and is administered intravenously.

What is claimed is:

1. A Steroid ester of the formula:

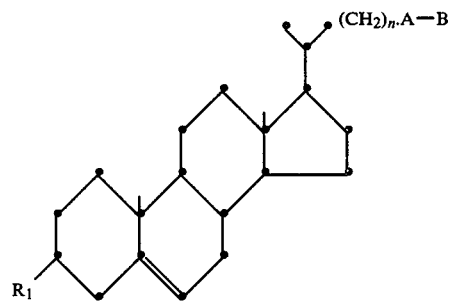

wherein

R₁ is an unsaturated aliphatic carbonyloxy radical of from 12-30 carbon atoms n is an integer of from 1-3

A is a bivalent linking radical selected from (a)

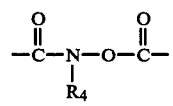

wherein R₄ is hydrogen lower alkyl, phenyl, or heteroaryl or (b)

(c)

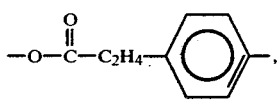

(d)

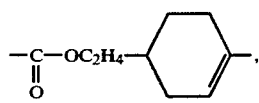

and

B is a monovalent radical of a cytotoxic substance linked through an amino nitrogen selected from bis-(2-chloroethyl)amine, uracil mustard, 6-mercaptopurine, thioquanine, adriamycin, procarbazine and mitomycin C.

2. A compound according to claim 1 wherein $R_1$ is selected from 3$\beta$-oleyoyloxy, 3$\beta$-linolenoyloxy, and 3$\beta$-linolenoyloxy radicals.

3. A compound according to claim 1 of the formula:

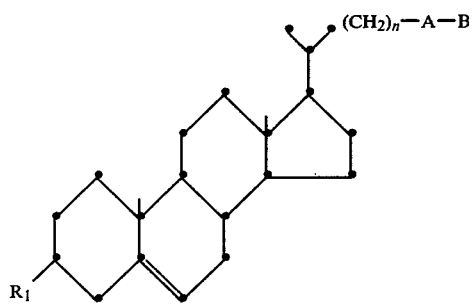

wherein A is defined in claim 1 B is a bis(2-chloroethylamino) radical of the formula —N(—CH$_2$CH$_2$Cl)$_2$.

4. A compound according to claim 1 which is 2-(3$\beta$-oleoyloxy-androst-5-en-17-yl)propyloxycarbonyl bis(2-chloroethyl)amine.

5. A compound according to claim 1 which is 4-(3$\beta$-oleoyloxy-androst-5-en-17-yl)pentyloxycarbonyl bis(2-chloroethylamine.

6. A process for the preparation of a compound of the formula:

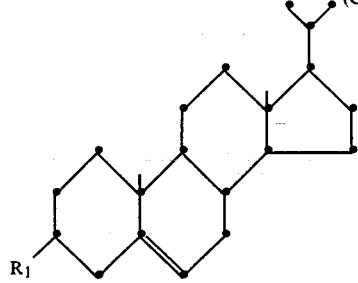

wherein $R_1$, n, A and B are defined as in claim 1 which comprises reacting together a steroid ester acid halide of the formula:

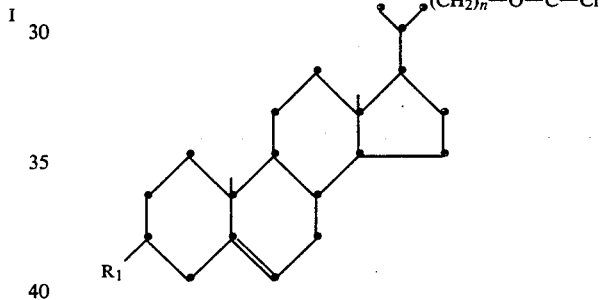

and a cytotoxic substance having a reactive amino substituent as defined in claim 1.

* * * * *